(12) United States Patent  
Umar (10) Patent No.: US 8,876,847 B2  
(45) Date of Patent: Nov. 4, 2014

(54) HAIR PUNCH (76) Inventor: Sanusi Umar, Redondo Beach, CA (US)

(*) Notice: Subject to any disclaimer, the term of this patent is extended or adjusted under 35 U.S.C. 154(b) by 335 days.

(21) Appl. No.: 12/978,965

(22) Filed: Dec. 27, 2010

(65) Prior Publication Data

US 2011/0160746 A1 Jun. 30, 2011

Related U.S. Application Data (60) Provisional application No. 61/291,761, filed on Dec. 31, 2009, provisional application No. 61/293,138, filed on Jan. 7, 2010, provisional application No. 61/363,378, filed on Jul. 12, 2010.

(51) Int. Cl.
A61B 17/14 (2006.01)
A61B 17/32 (2006.01)
A61B 17/3205 (2006.01)
A61B 17/00 (2006.01)

(52) U.S. Cl.
CPC . *A61B 17/32053* (2013.01); *A61B 2017/00752* (2013.01); *A61B 2017/320064* (2013.01)
USPC .......................................................... 606/184

(58) Field of Classification Search
CPC ............... A61B 17/32053; A61B 2017/00752; A61B 10/0266; A61B 17/32093; A61B 2017/00969; A61F 2/10
USPC .......... 606/131, 133, 167, 184; 600/564, 566, 600/567
See application file for complete search history.

(56) References Cited

U.S. PATENT DOCUMENTS

| | | | |
|---|---|---|---|
| 1,557,464 A * | 10/1925 | Mick | 408/205 |
| 5,792,163 A * | 8/1998 | Hitzig | 606/167 |
| 5,827,199 A | 10/1998 | Alexander | |
| 7,172,604 B2 | 2/2007 | Cole | |
| 2002/0052619 A1* | 5/2002 | Transue | 606/185 |
| 2005/0203545 A1 | 9/2005 | Cole | |
| 2005/0267506 A1 | 12/2005 | Harris | |
| 2006/0178677 A1 | 8/2006 | Brinson | |
| 2007/0156164 A1 | 7/2007 | Cole | |
| 2007/0213741 A1 | 9/2007 | Cole | |
| 2007/0293884 A9 | 12/2007 | Cole et al. | |
| 2008/0051805 A1 | 2/2008 | Pinchuk | |
| 2008/0051806 A1 | 2/2008 | Cole | |
| 2008/0234698 A1* | 9/2008 | Oostman et al. | 606/133 |
| 2009/0240261 A1 | 9/2009 | Drews | |
| 2009/0264795 A1* | 10/2009 | Dunn | 600/567 |

OTHER PUBLICATIONS

Written Opinion of International Searching Authority; Corresponding PCT Application No. US2010/062144 filed Dec. 27, 2010.

* cited by examiner

*Primary Examiner* — Katherine M Shi
(74) *Attorney, Agent, or Firm* — Robert A. Seldon (57) ABSTRACT

A punch for removing hair follicles from a donor site comprises a generally tubular body having a proximal end region terminating in a tissue-cutting edge, a distally-extending segment of reduced outer diameter—preferably a generally concave segment—terminating at its proximal end at or near the cutting edge and terminating at its distal end with a diameter substantially the same or greater than the diameter of the cutting edge. The punch further includes a follicle-receiving chamber defined by an inner wall extending distally from the proximal end of the punch. Preferably, at least a portion of the chamber lying within the external region of reduced diameter is generally converging in the distal direction.

34 Claims, 7 Drawing Sheets fig. 2 fig. 1

HAIR PUNCH

CLAIM OF PRIORITY

Priority is claimed of U.S. Provisional Patent Application 61/291,761 filed Dec. 31, 2009, U.S. Provisional Patent Application 61/293,138 filed Jan. 7, 2010, and U.S. Provisional Patent Application 61/363,378 filed Jul. 12, 2010, the contents of which are hereby incorporated by reference.

FIELD OF THE INVENTION

This invention relates to surgical instruments and, more particularly, to a punch for extracting hair follicles from the skin.

BACKGROUND OF THE INVENTION

Hair transplantation is a surgical technique that involves moving skin containing hair follicles from one part of the body (the donor site) to bald or balding parts (the recipient site).

Hair naturally grows in follicles that contain groupings of 1 to 4 hairs, and transplant techniques typically move the 1-4 hair "follicular units" from the donor site to the recipient site. The follicles of hair are typically removed from the donor site using punches of between 0.7 mm and 1.25 mm in diameter. The punches are tubular bodies having a skin-contacting cutting edge, and are typically mounted in a tool that causes the punch to rotate as the punch is brought into contact with the donor site. Hair follicles are very easily broken during the removal process, and broken follicles are unlikely to be successfully transplanted.

SUMMARY OF THE INVENTION

A punch for removing hair follicles from a donor site comprises a generally tubular body having a proximal end region terminating in a tissue-cutting edge, a distally-extending segment of reduced outer diameter—preferably a generally concave segment—terminating at its proximal end at or near the cutting edge, and terminating at its distal end with a diameter substantially the same or greater than the diameter of the cutting edge. The punch further includes a follicle-receiving chamber defined by an inner wall extending distally from the proximal end of the punch. Preferably, at least a portion of the chamber lying within the external region of reduced diameter is generally converging in the distal direction.

DESCRIPTION OF THE DRAWING

Of the detailed description to be described hereinbelow.

DETAILED DESCRIPTION OF THE PREFERRED EMBODIMENT

Figures 1, 2:
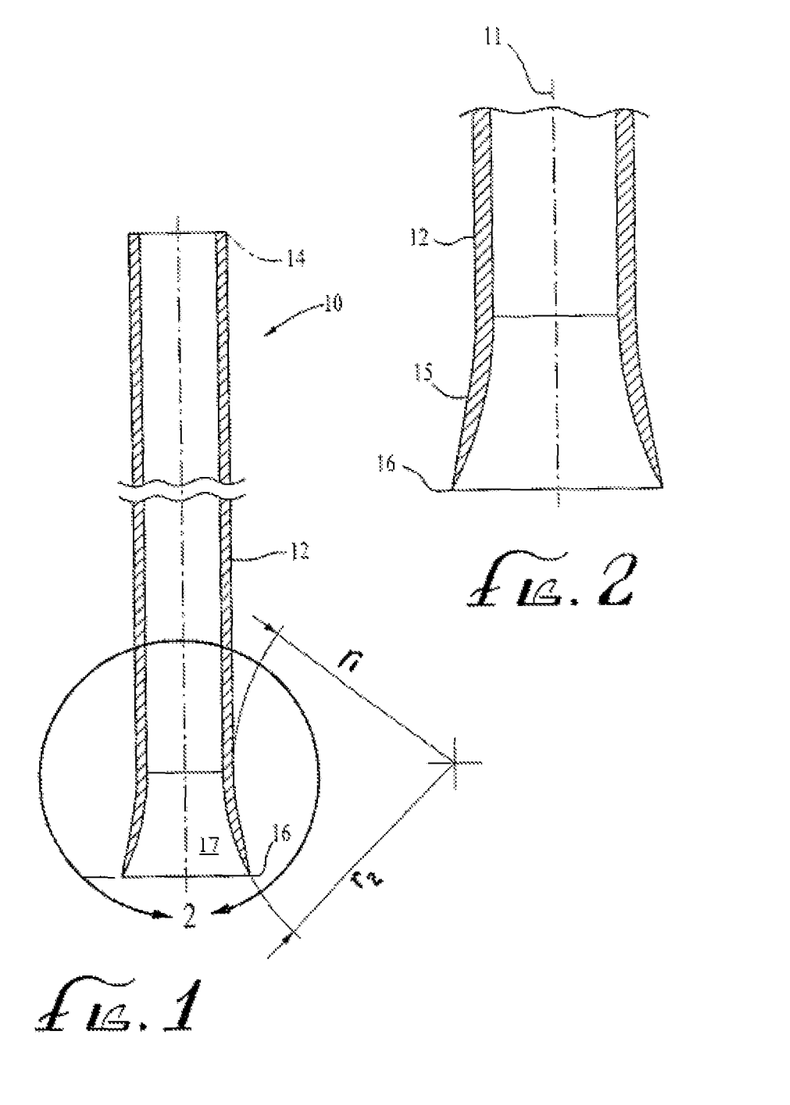
FIG. 1 is a longitudinal section view showing a punch for removing hair follicles that is constructed in accordance with the invention.
FIG. 2 is an enlarged fragmentary view of the portion of the punch illustrated within the line 2 of FIG. 1.

FIG. 1 is a longitudinal section view showing a punch 10 for removing hair follicles that is constructed in accordance with the invention, and FIG. 2 is an enlarged fragmentary view of the portion of the punch illustrated within the line 2 of FIG. 1. Although such punches can be used with a manual device, their optimal application is achieved when mounted on a rotary device.

As illustrated in FIGS. 1 and 2, the punch 10 comprises a generally tubular body 12 extending from a distal end 14 to a skin-contacting proximal end 16 about a generally central longitudinally-extending axis 11, and having a follicle-receiving chamber 17. As used herein, the phrase "lateral surface of the body" is used in relation to axis 11 to refer to a surface of the punch that is radially spaced from the axis." The illustrated punch is characterized by a flared proximal end region 15 having a diverging inner diameter and diverging outer diameter along the last 1 mm or so as measured from the distal end. The flared end region terminates at the proximal end in a skin-contacting cutting edge of approximately 0.5 to 1.2 mm in diameter. Preferably, the punch is sharpened from the inside to form the cutting edge at its proximal end. However, the punch can be sharpened from the outside to form the cutting edge without departing from the scope of the invention. The preferred the cutting edge is formed by the convergence of the punch's outer surface and the chamber wall at an approximately 9.8° angle of convergence. The angle, however, can be as small as approximately 4° or as large as approximately 20°, but 9.8° is currently preferred in connection with this configuration.

Hair follicles are easily damaged during the removal procedure at the donor site by frictional contact with the interior wall of the rotating punch, and by the punch's cutting edge as it descends into the tissue. With respect to the frictional damage, there can come a point during the removal at which the follicle becomes impacted against the inner wall of a conventional punch to such an extent that the follicle rotates with the punch as essentially a single unit as the graft is gathered into the chamber. In the mean time, the opposite end of the follicle remains relatively substantially stationery, resulting in a twisting of the follicle until said opposite end is sheared off. This is called "transection". The two transected parts of the follicle are less viable, and unsuitable for transplantation.

The shape of the chamber within a punch constructed in accordance with the invention, however, tends to permit the punch to rotate smoothly around the follicle. The shape of the chamber distal to the cutting edge of the punch increases the capacity of the punch lumen, thus reducing the friction between follicle and the punch's inner wall. Consequently there is less temperature build-up, less damage to the follicular tissue, less incidence of impaction and, consequently, a reduction in the transection rate.

Figures 12A, 12B:
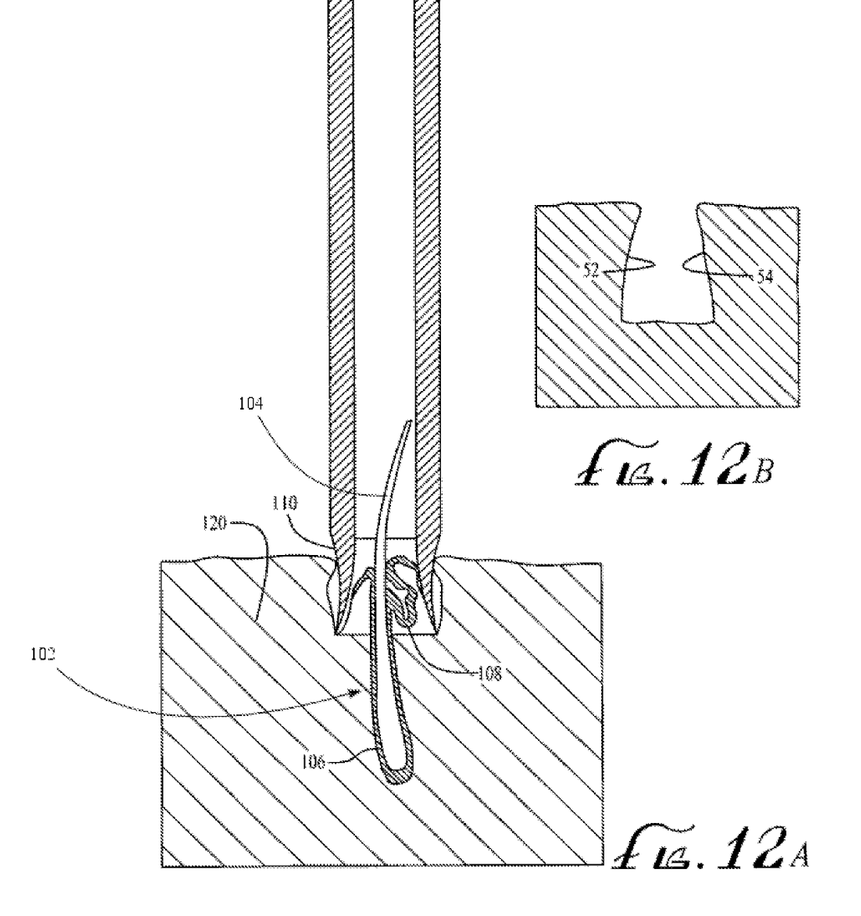
FIG. 12a is a schematic illustration of a hair follicle being extracted with a punch constructed in accordance with the invention.
FIG. 12b is a schematic illustration of the wound preferably created from the use of a punch constructed in accordance with the invention.

Moreover, the flare in the proximal end region of the punch herein results in a significant improvement in this microsurgical application. FIG. 12a schematically illustrates the manner by which a punch constructed in accordance with the invention reduces friction-induced transection, and yields a relatively bulky graft as well. A hair follicle 102 is illustrated imbedded in tissue 120 at the donor site just prior to extraction. The follicle illustratively comprises a hair 104, hair root 106 and sebaceous gland 108. The flared proximal end region 110 of the punch circumscribes the follicle. Because the proximal end region of the punch is flared, there is less chance of transection of the follicle in the event the punch and follicle are not perfectly aligned laterally or angularly during punch insertion.

The flared proximal end region, and the slant of the cutting edge, improve the ability of the punch to gather the hair follicle and extract it with minimal or no damage to the follicle. As the tissue at the donor site is entered by the rotating punch, the tissue surrounding the punch's outer diameter must transition away from the follicle and over the flared end region of the punch. The result is a smooth transition as the outer diameter of the punch encountered by the surrounding tissue decreases with insertion of the punch, and as the preferred interior sharpening of the cutting edge creates cutting pressure in a direction away from the hair follicle rather than towards the follicle. There is accordingly a decrease in stress on the follicle and a reduction in the chance of damage thereto as the follicle enters the punch and is supported therein by the punch's gently converging inner wall. The cutting pressure is not only away from the follicle, but is also thereby directed into the surrounding tissue, leading to a larger tissue investment around the follicle. The result is the production of bulkier follicles.

Bulkier follicles have substantially all components essential for regeneration upon transplantation compared to slimmer follicles. Also, bulkier follicles are more resilient and less subject to destructive forces such as desiccation on exposure to the elements and trauma from rough handling, because the robust tissue investiture imparts a protective shield around the vital structures of the follicle that are required for regeneration. It may be noted that desiccation of follicles before transplantation is the major cause of failed hair transplants due to poor graft take (i.e., a major cause of "low yield").

The bulkier bundle of tissue entering the punch, vis-à-vis conventional punches, together with the preferred chamber shape described above, results in more cushioning of the sebaceous gland and hair root from trauma during extraction and handling, and yields a greater chance of survival after implantation. By contrast, follicles obtained with conventional punches have been more slender, with less surrounding tissue, drier, and more susceptible to damage.

Another advantage imparted by the punch 10 is that the wound created by the punch has a tendency to heal more quickly than wounds arising from the use of currently available punches. The flared end of the punch 10 creates a wound whose diameter narrows distally, resulting in a wound with inverted edges 52, 54 (FIG. 12(b)); i.e., with a generally triangular vertical section (as oriented in FIG. 12(b)) extending distally towards an apex. Conventional punches create wounds that are cylindrical with parallel or even everted edges. When allowed to heal by secondary intention (i.e., the healing of a wound by granulation after suppuration), wounds with inverted edges heal faster with better cosmesis compared to wounds with parallel or everted edges. In body and beard hair extraction this becomes vitally important as the wounds are not hidden by surrounding hair (as is the case with the scalp). A balance has to be struck between generating viable fat follicles and faster/better wound healing and cosmesis.

In summary, use of a punch constructed as described herein is believed to result in less chance of transection, a faster-healing wound with less or no visible scarring, and a higher chance of follicle survival than previously obtained with conventional punches.

Figures 3, 4:
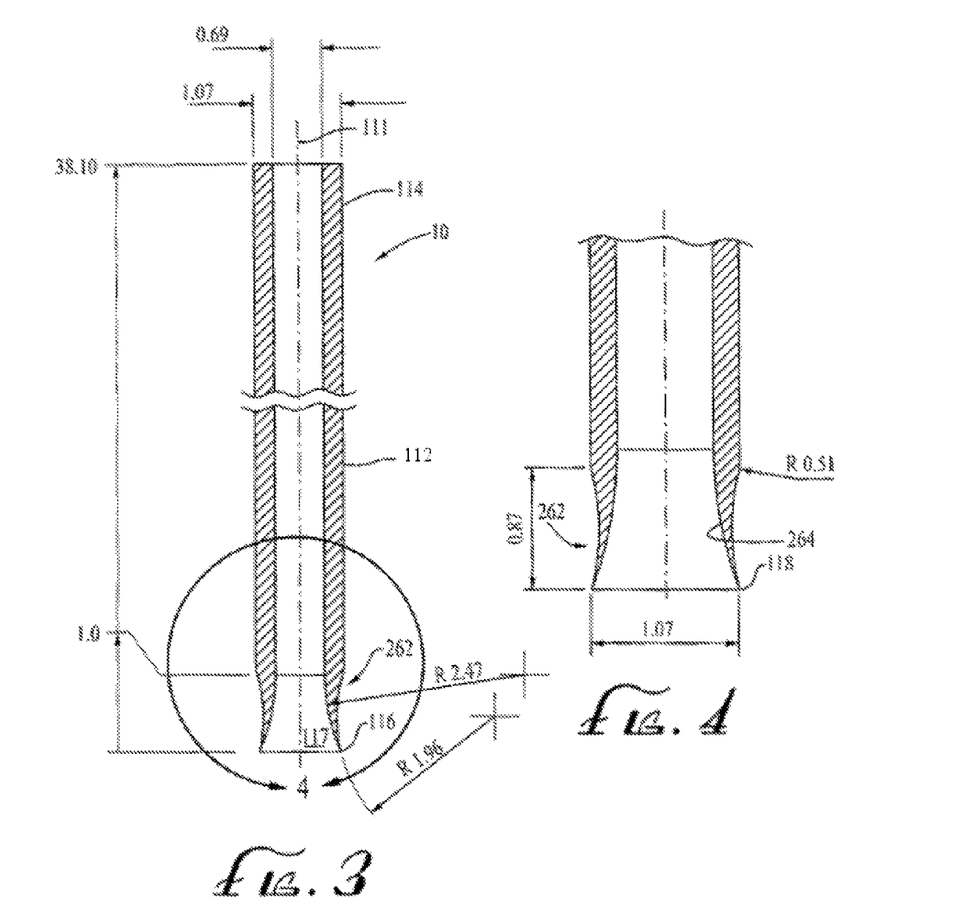
FIG. 3 is a longitudinal section view showing the specific configuration of the presently preferred punch.
FIG. 4 is an enlarged fragmentary view of the portion of the punch illustrated within the line 4 of FIG. 3.

FIG. 3 is a longitudinal section view showing the specific configuration and preferred dimensions of the presently preferred punch 10, while FIG. 4 is an enlarged fragmentary view of the portion of the punch illustrated within the line 4 of FIG. 3. For the sake of clarity and efficient understanding, the presently preferred dimensions of the punch are illustrated in FIGS. 3 and 4, although those skilled in the art will recognize that these dimensions can be varied without departing from the scope of this invention.

The punch illustrated in FIGS. 3 and 4 comprises a generally cylindrical body 112 formed about a generally central axis 111 and extending from a proximal cutting end 116 to a distal end 114. The body has a follicle-receiving chamber 117 extending distally from the proximal cutting end. The chamber preferably converges in the distal direction, but can also be non-diverging without departing from the invention. While the punch illustrated in FIG. 3 shows the chamber extending from the proximal end of the punch to the distal end of the punch, those of ordinary skill in the art will realize that it need not extend to the distal end so long as there is sufficient depth to the chamber to permit the capture of the extracted follicle and, preferably, a path for permitting the egress of displaced air as the follicle enters the chamber.

The proximal end of the punch has a cutting edge 118 which may be unsharpened or, preferably, sharpened. The cutting edge may be sharpened from the exterior of the punch or, as preferred for reasons explained later, from the inside.

Figure 13:
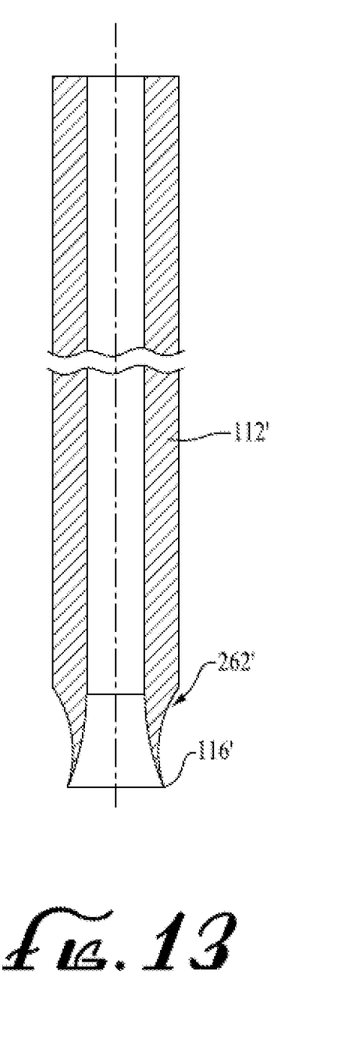
FIG. 13 is a longitudinal section view of an alternative punch that is a variation of the punch illustration in FIG. 3.

A portion of the tubular body distal to the proximal end has an external segment of reduced diameter in the form of generally concave exterior shape 262 extending distally from the proximal end of the punch. While a substantially smooth concave segment is preferred, the segment can alternatively be stepped or angled without departing from the scope of the invention, and these variations are intended to be included within the term "concave" as used herein. Preferably, the outer diameter of the punch is generally the same at the beginning and end of the segment. In practice, there may be a slight difference in the two when the intent is to make them identical, and the skilled in the art will further recognize that the diameter of the punch at the segment's distal end can be greater than the punch's diameter at the segment's proximal end, as illustrated by way of example in FIG. 13 wherein the outer diameter of punch body 112' above the concave region 262' is greater than the outer diameter at the cutting edge 116', without departing from the scope of invention. Also, while the proximal end of the segment preferably terminates at the cutting edge as illustrated in FIGS. 3 and 4, it may alternatively terminate just distal of the cutting edge without departing from the scope of the invention. The concavity in the preferred segment can most easily be formed by grinding it into an initially cylindrical punch body.

The concave shape serves two purposes. First, its preferred size and shape results in a wound with inverted edges; as the punch enters the tissue surrounding the targeted follicle, the tissue outward of the cut expands against the concavity as it is passed by the cutting edge. When the punch is subsequently withdrawn, the tissue resumes its consequently inverted shape.

Secondly, the concave shape and preferred sharpening from the inside of the punch results in a cutting force that is outwardly directed away from the follicle and tissue to be extracted. In its preferred form, the cutting edge is defined by the joining of the interior cavity wall and exterior punch surface so that two surfaces diverge from each other at an angle in the range of approximately 4° to approximately 20°.

In the illustrated embodiment of FIGS. 3 and 4, the portion of the preferred punch extending distally from the proximal end has a concave shape characterized by radius of curvature R1 of approximately 0.077 inches (1.96 mm) that extends approximately 0.0344 inches (0.87 mm) distally from the proximal end of the punch (L3), with the punch's outer diameter at the proximal end being approximately that of its outer diameter at the distal end (d1). The interior wall of the illustrated punch diverges in the proximal direction, starting approximately 0.039 inches (1 mm) from the proximal end, along a gentle arc (R2) of 0.097 inches (2.47 mm).

The illustrated punch, itself, has an outer diameter (d1) of 0.042 inches (1.07 mm) from its distal end to the distal end of the concave region.

The illustrated punch's internal diameter (d2) is approximately 0.0270 inches (0.69 mm) from its distal end to the point at which the interior wall begins to diverge.

The cutting edge formed at the proximal end of the punch is characterized by a preferred angle of convergence (referred to in the table below as θ) of approximately 9.8° between the punch's outer surface and the chamber wall.

The sizes and relative proportion of the dimensions may vary depending on such factors as the outer diameter d1 of the punch and the size of the follicle to be extracted; in some cases, it may be a hair plug that is to be extracted and/or implanted. Accordingly, the dimensions of punches constructed in accordance with the configuration shown in FIGS. 3 and 4 may vary from the example illustrated and described herein, Thus, the interior wall of the follicle-receiving cavity distal to where its interior wall begins to diverge may have a diameter (d2) of 0.3 and 4.75 mm for punches having an outer diameter (d1) of 0.5 mm and 5.0 mm respectively, with the two diameters being similarly proportioned for outer diameters therebetween. The angle of the sharpened cutting edge may be in the range of approximately 4° to approximately 20°.

There are a number of punch configurations that have proven less optimal. Returning to FIGS. 1 and 2, the flare of that punch's outer diameter can, in one variant, be a gentle arc $r_1$ of approximately 0.0846 to 0.0884 inches (2.15 to 2.25 mm) commencing approximately 0.039 inches (1 mm) from the proximal end 16 Alternatively, the arc can have a radius of approximately 0.0884 inches (2.25 mm) over approximately the first 0.02 inches (0.5 mm) of axial length from the proximal end towards the distal end, and gently transform to an arc having a radius of approximately 0.0846 inches (2.15 mm) for approximately 0.02 inches (0.5 mm) of additional axial length towards the distal end.

The preferred internal diameter of this first variant transitions from approximately 0.047 inches (1.2 mm) at the proximal end 16 to approximately 0.028 inches (0.7 mm) within 0.04 inches of axial length, while the outer diameter transitions from approximately 0.028 inches (i.e., approximately the same dimension as the internal diameter to define a cutting edge) to 0.0357 inches (0.9 mm) within that 0.04 inches of length.

Figure 5:
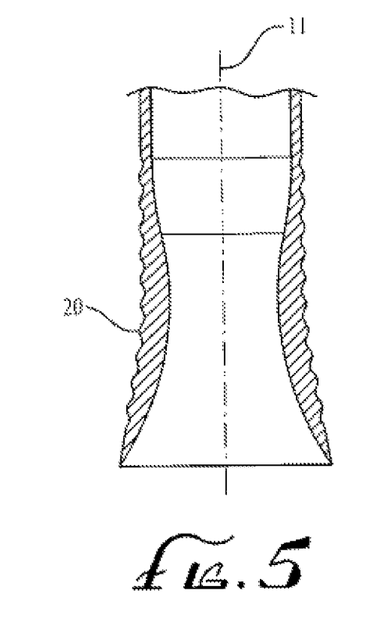
FIG. 5 is a fragmentary longitudinal sectional view showing a punch constructed in accordance with the invention and having an external textured region.
Figure 6:
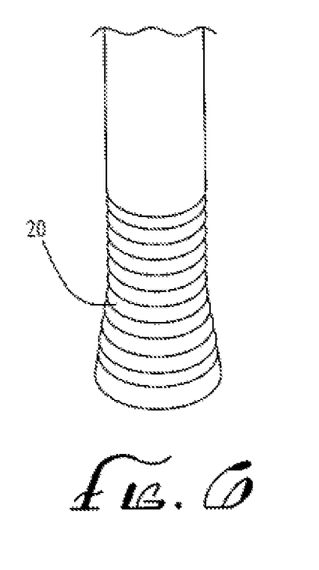
FIG. 6 is a fragmentary front elevation view of the punch of FIG. 5.

Preferably, the proximal end region of a punch constructed in accordance with the invention is provided with a textured exterior region 20, as illustrated in FIG. 5. As the rotating punch is pushed into the tissue, the textured region appear to enhance the suction-like effect that gently sucks the cut tissue towards the punch as it descends into the tissue, and thereby helps to impart the everted edges to the wound. It is believed that the texture creates mini vortices that impart a suction effect on the tissue surrounding a fast rotating punch. The currently preferred textured region is composed of thin lines of surface discontinuity approximately 12.5 micrometers deep and spaced approximately 0.15 mm apart. Those skilled in the art will recognize that the "lines" need not necessarily be straight or continuous, and may comprise separated surface discontinuities following some pattern or arranged in a relatively random manner. Although the presently preferred textured region illustrated in FIGS. 5 and 6 is comprised of lines that are concentric about axis 11 and extend 360° about the punch, the textured region may instead comprise lines that are helical and/or extend less than 360°. Further, the textured region may be continuous or may be formed in separate spaced-apart circular or helical segments so long as the desired effect is achieved. Moreover, the textured region can instead comprise randomly distributed discontinuities in the surface of the punch. The textured region preferably extends to the cutting edge, but can be slightly spaced therefrom if one wishes to do so.

Punches constructed in accordance with the invention can also include an internal textured region instead of, or in addition to, the textured external region described above. The interior textured region appears to help draw the follicle into the chamber; it is believed that, like the external texture, the interior texture creates mini-vortices that impart a suction effect on the tissue follicle. Preferably, the punch has both a textured external region and an internal textured region.

Figure 7:
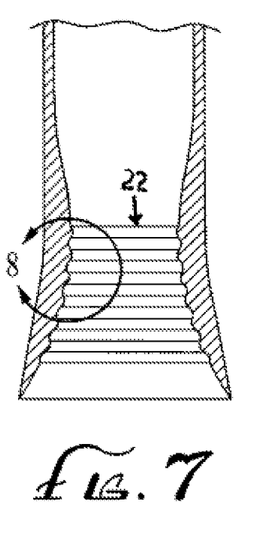
FIG. 7 is a fragmentary sectional view showing a punch constructed in accordance with the invention and having an internal textured region.
Figure 8:
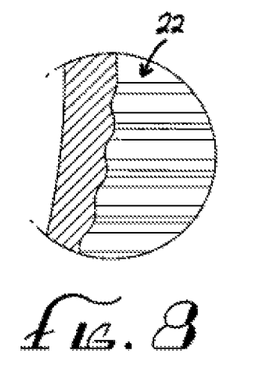
FIG. 8 is an enlarged detail view showing the region within the line 8 of the punch in FIG. 7.

The presently preferred internal textured region 22 illustrated in FIGS. 7 and 8, preferably comprises surface discontinuities of the same size and spacing as the exterior textured region, and is disposed over at least a part of the diverging interior portion of the punch. As with the exterior textured region, the interior textured region can comprise concentric lines that extend 360° about the punch, are helical and/or extend less than 360°. Further, the internal textured region can be continuous or formed in separate spaced-apart circular or helical segments, or comprise randomly distributed discontinuities in the wall of the follicle-receiving chamber, so long as the desired effect is achieved. Currently, the preferable configuration is on which utilizes concentric interior and exterior lines that extend 360° about the punch. Preferably, the textured region extends to the cutting edge, but can be slightly spaced therefrom if one wishes to do so.

Figure 9:
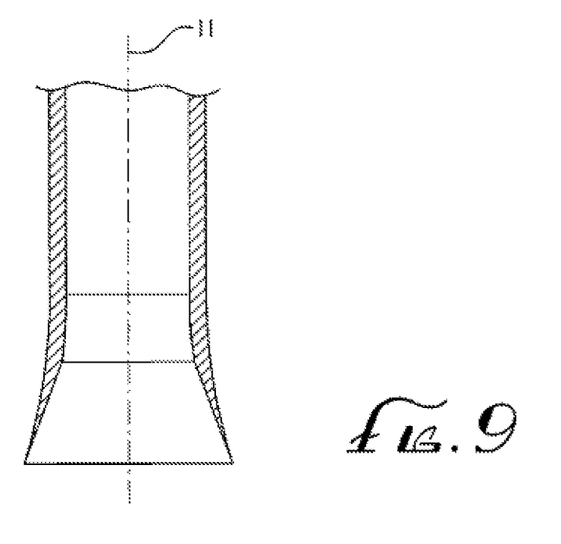
FIG. 9 is a fragmentary sectional view showing another variant of a punch constructed in accordance with the invention.

FIG. 9 illustrates another variant of a punch constructed in accordance with the invention. In this variant, the divergence of the punch's interior wall within the flared end region is generally linear rather than curved. Preferably, the interior wall diverges at an angle of about 20° from the punch's longitudinal axis 11, although a steeper or shallower angle that accomplishes generally the same effect is within the scope of this invention. The outer diameter of the illustrated flared portion in FIG. 9 preferably diverges as an arc having approximately a 0.154 inch (3.90 mm) radius.

Figures 10, 11:
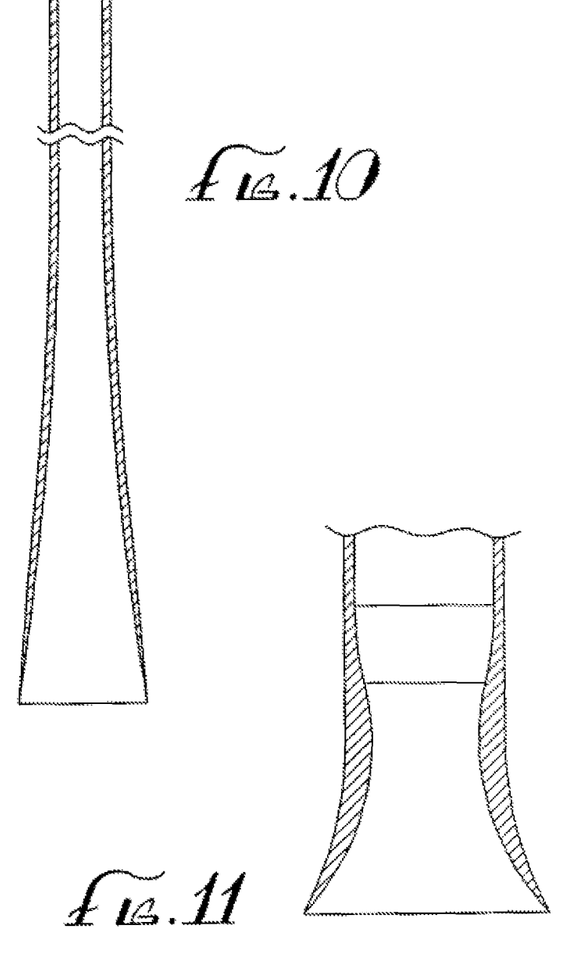
FIG. 10 is a longitudinal sectional view showing another punch constructed in accordance with the invention.
FIG. 11 is a fragmentary sectional view of another punch constructed in accordance with the invention.

FIG. 10 illustrates another variant of a punch constructed in accordance with the invention. Here, the flare starts further from the proximal end of the punch and the both the internal and external diameters of the punch change more gently. In the punch of FIG. 10, the flare begins approximately 0.20 inches (5.08 mm) from the proximal end of the punch. In one version, the external surface of the punch within the flared region is an arc of approximately 1.28 inches (32.64 mm) while the internal wall of the punch within the flared region is an arc of approximately 1.2881 inches (32.72 mm). The upward slant of the cutting edge associated with the external sharpening of the cutting edge is preferably approximately 4.7° with respect to the punch's longitudinal axis. In a second version, the external surface of the punch within the flared region is an arc of approximately 1.60 inches (40.73 mm) while the internal wall of the punch within the flared region is an arc of approximately 1.6065 inches (0.81 mm), with an angle of 10°. These are exemplary dimensions, however, and those of ordinary skill in the art will realize that the dimensions can be modified to obtain desired results.

FIG. 11 illustrates another variant of a punch constructed in accordance with the invention. Here, the internal wall of the punch is almost hour-glass shaped. As the follicle enters the punch, it is gently and increasingly supported as the internal diameter of the punch's internal cavity decreases for the first 0.04 inches or so. By way of example, the internal diameter illustrated in FIG. 11 decreases from 0.055 inches to 0.024 inches over the first 0.0394 inches from the proximal end. The internal diameter then gently increases over the next 0.130 inches to 0.0270 inches and again over the next 0.172 inches to 0.0270 inches. This, in effect, creates a capacious chamber distal to the cutting end that serves to gather the building follicular tissue mass as it is pulled distally into the lumen of the punch. This chamber is designed to inhibit an increasing volume of follicular tissue from building up in the narrower lumen of the punch, leading to increased friction between the follicular tissue and the inner wall lining of the punch. Such increased friction, in turn, leads to an increased temperature build up that is damaging to the follicle, hence reducing its viability when transplanted.

Although the present invention and its advantages have been described in detail, it should be understood that various changes, substitutions and alterations can be made herein without departing from the spirit and scope of the invention as will be defined solely by appended claims.

I claim:

1. A punch for removing targeted hair follicles from surrounding body tissue, and comprising:
    a generally cylindrical body formed about a generally central axis and extending distally from a proximal cutting end,
    the body having a follicle-receiving chamber defined by an interior wall within the generally cylindrical body extending distally from the proximal cutting end,
    the proximal cutting end of the punch having a generally curved concave exterior segment on a lateral surface of the generally cylindrical body, the generally curved concave exterior segment terminating proximally in a cutting edge having an outer diameter selected from the range of approximately 0.5 to approximately 5 mm,
    the generally curved concave exterior segment positioned so that tissue surrounding the targeted follicles outward of the cutting edge can expand against the concavity as the tissue is passed by the cutting edge to yield a substantially-inverted wound upon follicle extraction.

2. The punch of claim 1 wherein at least a portion of the follicle-receiving chamber is within the generally curved concave exterior segment of the body and converges in the distal direction.

3. The punch of claim 1 wherein the generally curved concave exterior segment extends along approximately the first 0.5 to 2 mm of the punch's axial length from the cutting end.

4. The punch of claim 1 wherein the generally curved concave exterior segment of the body extends along approximately the first 0.87 mm of the punch's axial length from the cutting end.

5. The punch of claim 1 wherein the cutting edge is in the range of approximately 0.8 to approximately 1 mm in diameter.

6. The punch of claim 1 wherein the proximal end of the punch is sharpened from the inside of the proximal end to form the cutting edge so that the sharpened proximal end exerts pressure in said surrounding tissue in a direction away from the targeted follicles as the cutting edge enters the surrounding tissue.

7. The punch of claim 6 wherein the cutting edge is defined by the interior wall and the generally curved concave exterior segment that diverge at an angle in the range of approximately 4° to approximately 20°.

8. The punch of claim 6 wherein the cutting edge is defined by the interior wall and the generally curved concave exterior segment that diverge at an angle of approximately 9.8°.

9. The punch of claim 1 wherein the cutting edge is shaped to direct a cutting force of the cutting edge away from the targeted follicles as the cutting edge cuts tissue surrounding the targeted follicles.

10. The punch of claim 1 wherein the generally curved concave exterior segment is characterized by a radius of curvature of approximately 0.077 inches (1.96 mm).

11. The punch of claim 1 wherein the interior wall converges from the proximal end to approximately 0.5 to 2 mm from the proximal end.

12. The punch of claim 1 wherein the interior wall converges along an arc of approximately 0.097 inches (2.47 mm).

13. The punch of claim 1 wherein the punch has an outer diameter distal to the commencement of the generally curved concave exterior segment selected from a range of diameters of approximately 0.5 to 5 mm.

14. The punch of claim 1 wherein the interior wall and the generally curved concave exterior segment diverge from the cutting edge in a distal direction, and wherein the generally cylindrical body has an internal diameter distal to where the interior wall begins to diverge selected from a range of diameters of approximately 0.3 to 4.75 mm.

15. The punch of claim 1 wherein the cutting edge is sharpened and defined by the interior wall and the generally curved concave exterior segment that diverge at an angle in the range of approximately 4° to approximately 20°.

16. The punch of claim 1 wherein the cutting edge is sharpened and defined by the interior wall and the generally curved concave exterior segment that diverge at an angle of approximately 9.8°.

17. The punch of claim 1 wherein the proximal end region of the punch has an exterior textured region that does not extend through the thickness of the generally cylindrical body.

18. The punch of claim 17 wherein the textured region is composed of lines of discontinuities approximately 12.5 micrometers deep.

19. The punch of claim 18 wherein the lines of discontinuities are generally concentric about the generally central axis.

20. The punch of claim 17 wherein the textured region includes generally lines of discontinuities that are approximately 0.15 mm apart.

21. The punch of claim 17 wherein the textured region extends approximately 360° about the punch.

22. The punch of claim 17 wherein the textured region is formed by discontinuous areas of surface discontinuity.

23. The punch of claim 17 wherein the textured region comprises generally helical lines of discontinuities in the external surface of the punch.

24. The punch of claim 1 wherein the proximal end region of the punch has an internal textured region that does not extend through the thickness of the generally cylindrical body.

25. The punch of claim 24 wherein the internal textured region comprises lines of discontinuities in an internal surface of the follicle-receiving chamber.

26. The punch of claim 25 wherein the lines extend substantially 360° around the chamber.

27. The punch of claim 25 wherein the lines are approximately 12.5 micrometers deep.

28. The punch of claim 25 wherein the lines are approximately 0.15 mm apart.

29. The punch of claim 1 wherein the generally curved concave exterior segment has proximal and distal ends of substantially equal outer diameter.

30. A punch for removing hair follicles from a donor site comprising:
a generally tubular body extending from a distal end to a flared proximal end about a generally central axis and having a follicle-receiving chamber extending distally from its proximal end,
the proximal end of the punch having a generally circular cutting edge having a diameter selected from the range of approximately 0.5 to approximately 5.0 mm in diameter,
at least a portion of the tubular body having a generally curved concave exterior segment on a lateral surface of the generally tubular body extending distally from the proximal end to impart a wound with generally inverted edges at the donor site,
at least a portion of the follicle-receiving chamber being substantially circumscribed by the generally curved concave exterior segment of the body and having an inner wall that converges in the distal direction.

31. The punch of claim 30 wherein the punch is sharpened from the inside of the proximal end to provide the cutting edge with an outward slant.

32. The punch of claim 30 wherein the cutting edge is formed by a convergence of the inner wall and the body's exterior at an angle of convergence selected from the range of approximately 4° to approximately 20°.

33. The punch of claim 30 wherein the punch is sharpened from the inside proximal end to define a cutting edge formed by a convergence of the inner wall and the body's exterior at an angle of convergence of approximately 9.8°.

34. The punch of claim 30 wherein the generally curved concave exterior segment is characterized by radius of curvature of approximately 0.077 inches (1.96 mm).

* * * * *